(12) United States Patent
Legrand

(10) Patent No.: US 6,280,675 B1
(45) Date of Patent: Aug. 28, 2001

(54) GROUTING METHOD FOR RIGIDLY CONNECTING TWO ELEMENTS USING A BINDER, AND IN PARTICULAR FOR ANCHORING ONE ELEMENT IN ANOTHER

(75) Inventor: Jean-Jacques Legrand, Chambery (FR)

(73) Assignee: Proseal (FR)

( * ) Notice: Subject to any disclaimer, the term of this patent is extended or adjusted under 35 U.S.C. 154(b) by 0 days.

(21) Appl. No.: 08/304,423

(22) Filed: Sep. 12, 1994

Related U.S. Application Data

(63) Continuation of application No. 07/983,512, filed on Mar. 1, 1993, now abandoned.

(30) Foreign Application Priority Data

Apr. 30, 1991 (FR) .................................................. 90/05557

(51) Int. Cl.[7] .......................... B29C 33/30; B29C 33/44; B29C 43/18; A61F 2/30
(52) U.S. Cl. .......................... 264/262; 264/261; 264/267; 264/273; 264/274; 606/92; 606/95
(58) Field of Search .................................... 264/259, 261, 264/274, 275, 277, 278, 294, 328.1, 39, 334, 273, 267, 262; 623/18, 22, 23; 606/92, 95

(56) References Cited

U.S. PATENT DOCUMENTS

| | | | |
|---|---|---|---|
| 3,920,787 | * 11/1975 | McDowell et al. | 264/263 |
| 4,157,369 | * 6/1979 | Doyle | 264/261 |
| 4,274,163 | * 6/1981 | Malcom et al. | 623/18 X |
| 4,562,598 | * 1/1986 | Kranz | 623/22 |
| 4,563,778 | * 1/1986 | Roche et al. | 623/22 |
| 4,653,489 | * 3/1987 | Tronzo | 606/65 |
| 4,718,909 | 1/1988 | Brown | 623/16 |
| 4,876,915 | * 10/1989 | Iuchi | 264/271.1 |
| 4,892,550 | * 1/1990 | Huebsch | 623/22 |
| 4,919,679 | 4/1990 | Averill et al. | 623/23 |
| 4,955,325 | * 9/1990 | Zarnowski et al. | 623/22 |
| 4,985,191 | * 1/1991 | Hannon, Jr. | 264/263 |
| 4,994,085 | * 2/1991 | Sawai et al. | 623/23 |
| 5,041,141 | * 8/1991 | Ypma et al. | 623/23 |
| 5,078,746 | * 1/1992 | Garner | 623/16 |
| 5,340,362 | 8/1994 | Carbone . | |

FOREIGN PATENT DOCUMENTS

| | | | |
|---|---|---|---|
| 3937786 | 7/1990 | (DE) . | |
| 0393425 | 10/1990 | (EP) . | |
| 0434604 | * 6/1991 | (EP) | 623/23 |
| 2662931 | * 12/1991 | (FR) | 623/18 |

\* cited by examiner

*Primary Examiner*—Angela Ortiz
(74) *Attorney, Agent, or Firm*—Ostrolenk, Faber, Gerb & Soffen

(57) ABSTRACT

A method of grouting which permits the joining together of two parts by means of a binder and, more particularly, the sealing of one part in another, in particular the sealing of a prosthesis in a bone cavity. The method includes producing in the part to be sealed a channel which passes through the part along an axis substantially parallel to the axis of the introduction of the part to be sealed into the recess formed in the part intended to receive it, and injecting the binder into the channel until the binder fills the space between the part and the wall of the recess. Centering elements can be placed around the part in the space present between the part and the wall of the recess, and a packing part can be positioned, around the part to be sealed, on the opening of the recess. The injection channel made in the part which is to be sealed can be provided with a thread which makes it possible to introduce a threaded rod into it for the extraction of the part.

3 Claims, 2 Drawing Sheets

GROUTING METHOD FOR RIGIDLY CONNECTING TWO ELEMENTS USING A BINDER, AND IN PARTICULAR FOR ANCHORING ONE ELEMENT IN ANOTHER

This is a Continuation of application Ser. No. 07/983,512 filed on Mar. 1, 1993, now abandoned.

BACKGROUND OF THE INVENTION

1. Field of the Invention

The object of the present invention is a method of grouting which makes it possible to join together two parts by means of a binder the consistency of which permits either a rigid or a flexible fastening and, more particularly, the sealing of one part in another, whether in the field of masonry, carpentry, industry or medicine, such as bone and dental surgery, for the sealing of a prosthesis.

2. Description of the Related Prior Art

Two methods are currently employed when it is desired to seal one part in another part, which has a recess adapted to receive the first part by means of a binder which makes it possible to effect the joining together of the parts: One consists in introducing the part to be sealed into the recess in the other part and filling the empty space by distributing the binder therein, while the other consists in filling the recess with binder and then introducing the part to be sealed before the binder has hardened.

Both of these methods have drawbacks. The first, in fact, does not make it possible to obtain perfect distribution of the binder so that air pockets, which are harmful to the good joining of the two parts, may be present. The second does not permit perfect positioning of the part to be sealed as there may be substantial differences in the thickness of the layer of binder and, furthermore, it entails the risk of stratification of the binder when the part to be sealed is pushed in. Furthermore, it is not easy to introduce into the recess that amount of binder which is precisely necessary to fill the empty space, with the result, if there is too much binder, of the surplus overflowing and, if there is not enough, the necessity to fill the remaining empty space by the method previously described, with the drawbacks indicated.

Furthermore, it is at times necessary to remove the sealed part, and this removal generally results in damage to the sealed part and/or the support part.

This is true, in particular, in the medical field of prostheses, since it is at times necessary to remove a prosthesis, for instance in case of an infection, and this implies not only extracting the prosthesis but also eliminating all of the binder which holds it and which may contain infectious germs. Now, this curettage operation is a very delicate one, entailing the risk that the tools used may cut into the bone caput. It is therefore necessary to take many precautions and to carry out careful and lengthy work, which is a great strain on the patient.

SUMMARY OF THE INVENTION

The present invention makes it possible to overcome these drawbacks by proposing a method of grouting and sealing which permits perfect positioning of the part to be sealed and perfect distribution of the binder in just the right amount, and which furthermore makes it possible, if necessary, to remove the sealed part more easily.

The method which is the object of the present invention consists in first of all producing in the part to be sealed a channel which passes through the part along an axis which is preferably substantially parallel to the axis of its introduction into the recess made in the support part, this channel making it possible, when the part to be sealed is maintained in the recess in its final position, to inject binder material from its outer orifice which material, after passing through the channel, spreads out between the part and the wall of the recess up to the outer edge of the recess.

The positioning of the part to be sealed in the recess can be facilitated by the use of spacers in the form of wedges or the like which block the part and assure a constant thickness of the covering of binder.

Furthermore, the injection channel can be provided with an internal thread, on the one hand to permit the attaching of a threaded element to the part and, on the other hand, to permit the removal of the sealed part by screwing a threaded rod into the channel down to the bottom of the recess.

BRIEF DESCRIPTION OF THE DRAWINGS

The advantages and characteristics of the present invention will become more clearly evident from the following description, read with reference to the accompanying drawings, which shows one embodiment thereof by way of illustration and not of limitation.

In the accompanying drawings.

DETAILED DESCRIPTION OF EMBODIMENTS OF THE INVENTION

Figure 1:
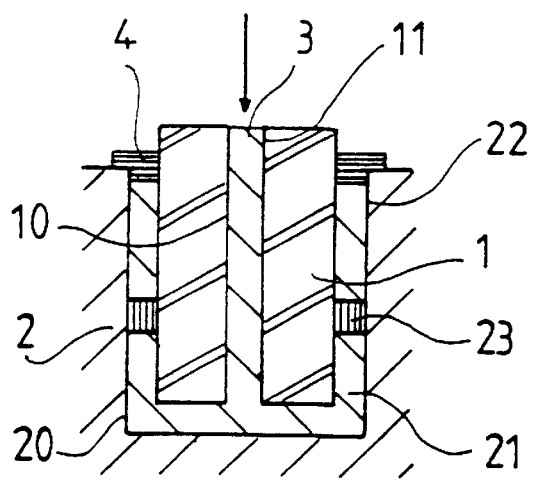
FIG. 1 is a diagrammatic view in section of a part sealed in another part by the method of the invention.

Referring to FIG. 1, there can be noted a part 1 sealed in a part 2 by means of the method of the invention. The part 1 has a channel 10, drilled axially in the direction of introduction of the part 1 into the recess 20 in the part 2. The part 1 is held by spacers 23 in the position which it is to occupy once sealed, whereupon the binder 3 is injected into the channel 10 from its outer opening 11, it spreading out in the channel 10 and then into the space 21 present between the part 1 and the wall of the recess 20, until reaching the edge 22 of the recess.

The edge 22 of the recess 20 can be provided with a packing part 4, which may have the shape of a collar, surrounding the part 1 and covering the space 21 so as to permit a better finish and create a certain tightness between the recess 20 and the part 1, so that upon the injection of the binder 3 resistance to the pressure is created, resulting in a better distribution of the binder 3.

In this way, particularly in the field of construction, it is possible, by providing an internal thread in the opening 11 of the channel 10, to fasten a threaded element in it without the fastening and sealing means being apparent.

The channel 10 produced in the part 1 also makes it possible to effect removal of binder from the bottom of conduit or tunnel without it being necessary to remove the part 1, as is generally the case. It is thus possible to test the aging of the binder, its physical-chemical modifications, etc.

Figure 2:
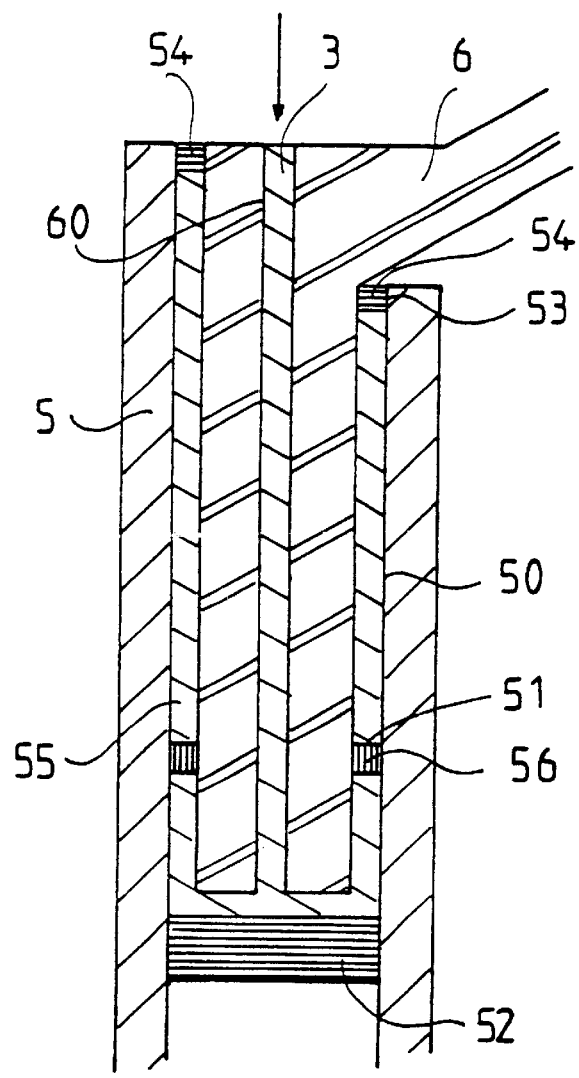
FIG. 2 is a diagrammatic view in section of the application of this method to the sealing of a femoral prosthesis.

Referring now to FIG. 2, there can be noted a femoral prosthesis 6 introduced and sealed into the medullary canal 50 of a femur 5 by the method according to the invention.

The femoral prosthesis 6 is traversed longitudinally in its center by a channel 60 and is held in the medullary canal 50 by means of centering elements 51 which can be formed of wedges or rings having orifices 56 the axes of which are parallel to the axis of the channel 60. The outer edge 53 of the medullary canal 50 can be provided with a provisional or final packing device 54 which, in the manner of the packing part 4 of FIG. 1, makes it possible to oppose resistance to the binder 3 injected into the channel 60 of the prosthesis 6 and which spreads out within the space 55 between the prosthesis 6 and the wall of the medullary canal 50, which is occluded by a diaphysial obturator 52.

This method of sealing a femoral prosthesis has the advantage, in addition to the ease and uniformity of positioning, of permitting the easy removal of the prosthesis in case of need, without risk of damaging the bone.

In fact, in order to remove this prosthesis 6 it is sufficient first of all to introduce a bit into the channel 60, drilling through the binder 3, until it traverses the diaphysial obturator 52. Then, as a second step, the prosthesis is removed, the end of the channel 60 being possibly provided with an internal thread so as to attach an extractor there. It is then merely necessary to remove the binder, which is an extremely delicate operation with the present-day methods. For this purpose, a rod can be introduced into the medullary canal 50 and the orifice made in the diaphysial obturator 52; this rod is centered and can serve as guide for bits having an axial channel through which the guide rod passes, and one can thus progressively bore until reaching the original diameters of the medullary canal without thereby damaging the bone caput either by false maneuvers or by enlarging the canal. One can thus position a new prosthesis with a saving in time and with less anesthesia and infection risks.

Figure 3:
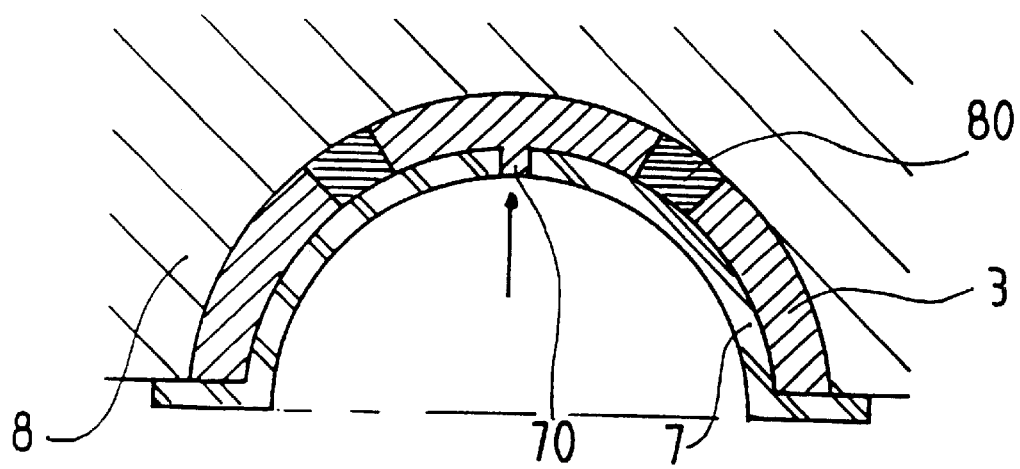
FIG. 3 is a diagrammatic view, in section, of the application of this method to the sealing of a cotyloid prosthesis.

Referring now to FIG. 3, it can be seen that the method of the present invention also makes it possible to seal a cotyloid prosthesis 7 in a cotyloid cavity 8. Ordinarily, the cavity 8 is filled with binder, whereupon the prosthesis, provide with spacers, is hammered in. However, the hammering forces the spacers into the bone of the cavity, which, on the one hand, makes the positioning of the prosthesis approximate and, on the other hand, results in the possibility of contact between the prosthesis and the cavity, and therefore less mechanical strength of the binder.

In accordance with this invention, an orifice 70 is made in the cotyloid prosthesis 7, which is provided with spacers 80 which permit its positioning, and the binder 3 is injected through the orifice 70. The position of the prosthesis 7 remains that which was initially established.

At present, in the event of a total hip prosthesis, the sealings of the two prostheses are effected one after the other, waiting for the setting of the binder of the first before sealing the second. Using the method of the invention, it is possible to position the two prostheses and at the same time effect the injection of binder, which permits a saving of time on the order of fifteen minutes, which is important for an operation.

Figure 4:
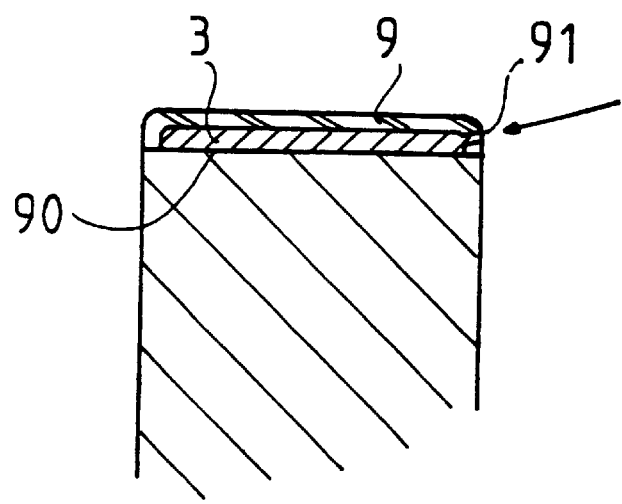
FIG. 4 is a diagrammatic view, in section, of the application of this method to the sealing of a total prosthesis in the cortico-spongiose region.

If one now refers to FIG. 4, it can be seen that the method of sealing in accordance with the invention can be applied to the positioning of all types of prostheses. In the case shown, the bone end is prepared by ephiphysial cut, for instance of a tibia, a prosthesis 9 is sealed on the tibial plateau 90 by injection of binder 3 through an orifice 91 made in the prosthesis 9. The amount of binder 3 is injected in the amount which is just necessary, so that it is no longer necessary to remover surplus binder, as must be done in accordance with the present methods, although these regions are particularly poorly accessible.

It goes without saying that the present invention is not limited to the applications and descriptions which have been set forth above, which may be subjected to a number of changes without thereby going beyond the scope of the invention.

What is claimed is:

1. A method of grouting to join together a first and second part by means of a binder, the second part having a recess therein, the recess having a bottom portion and a side portion, the method comprising the steps of:

(a) providing a channel in the first part which extends through said first part from a top surface to a bottom surface thereof, the channel formed in the first part being provided with a thread which permits the introduction therein of a threaded guide rod for the extraction of the first part, (b) inserting the first part with the bottom surface facing the bottom portion of the recess into the second part such that the first part is spaced from the bottom and the side portion of the recess, (c) injecting the binder into said channel to pass through said first part until said binder fills the space between the first part and the bottom and side portion of the recess, the binder filling the space by first filling the bottom portion and then rising upward in said space, (d) providing in the space between said first part and the side portion of the recess at least one centering element, the centering element defining means for passage of the binder as the binder rises upward in the space, and (e) positioning in the channel a threaded guide rod.

2. A method according to claim 1, further comprising the step of positioning a centering and finishing part around the first part, at the opening of the recess.

3. A method according to claim 1, further comprising the step of delivering the binder to a lower end of the first part, the binder rising upward from the lower end to fill the space.

* * * * *